United States Patent
Gan et al.

(10) Patent No.: US 6,569,442 B2
(45) Date of Patent: May 27, 2003

(54) PREPARATION OF POLYMER FOAM HAVING GELLED SOL COATING FOR INTERVERTEBRAL DISC REFORMATION

(75) Inventors: Jean Chin Chin Gan, Ardmore, PA (US); Paul Ducheyne, Rosemont, PA (US); Edward Vresilovic, Philadelphia, PA (US); Irving Shapiro, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/833,284

(22) Filed: Apr. 12, 2001

(65) Prior Publication Data

US 2001/0020476 A1 Sep. 13, 2001

Related U.S. Application Data

(62) Division of application No. 09/314,511, filed on May 19, 1999, now Pat. No. 6,240,926, which is a division of application No. 08/694,191, filed on Aug. 8, 1996, now Pat. No. 5,964,807.

(51) Int. Cl.[7] .......................... A61F 2/44; A01N 63/02; C12N 11/14; C12N 11/08; C12N 5/08
(52) U.S. Cl. ...................... 424/426; 128/898; 424/423; 424/93.7; 435/176; 435/177; 435/180; 435/325; 435/381; 435/395; 435/397; 623/17.16
(58) Field of Search ................................ 435/174, 176, 435/177, 180, 325, 378, 381, 395, 397; 424/93.7, 423, 426; 128/898; 623/17.16

(56) References Cited

U.S. PATENT DOCUMENTS

| | | | |
|---|---|---|---|
| 4,655,777 A | 4/1987 | Dunn et al. | 623/16 |
| 4,772,287 A | 9/1988 | Ray et al. | 623/17 |
| 4,904,206 A | 2/1990 | Ray et al. | 623/17 |
| 4,911,718 A | 3/1990 | Lee et al. | 623/17 |
| 5,002,576 A | 3/1991 | Fuhrmann et al. | 623/17 |
| 5,007,939 A | 4/1991 | Delcommune et al. | 623/66 |
| 5,035,713 A | 7/1991 | Friis | 623/16 |
| 5,041,138 A | 8/1991 | Vacanti et al. | 623/16 |
| 5,074,916 A | 12/1991 | Hench et al. | 623/16 |
| 5,084,051 A | 1/1992 | Tormala et al. | 623/16 |
| 5,108,438 A | 4/1992 | Stone | 623/17 |
| 5,204,104 A | 4/1993 | Bolinger et al. | 424/401 |
| 5,204,106 A | 4/1993 | Schepers et al. | 623/16 |
| 5,258,043 A | 11/1993 | Stone | 623/66 |
| 5,290,552 A | 3/1994 | Sierra et al. | 424/423 |
| 5,366,508 A | 11/1994 | Brekke | 623/16 |
| 5,376,118 A | 12/1994 | Kaplan et al. | 623/11 |
| 5,376,120 A | 12/1994 | Sarver et al. | 623/16 |
| 5,458,642 A | 10/1995 | Beer et al. | 623/17 |
| 5,478,739 A | 12/1995 | Slivka et al. | 106/35 |
| 5,591,453 A | * 1/1997 | Ducheyne et al. | 424/484 |
| 5,686,091 A | * 11/1997 | Leong et al. | 424/426 |
| 5,964,807 A | 10/1999 | Gan et al. | 623/17 |
| 6,240,926 B1 | 6/2001 | Chin Gan, et al. | 128/898 |

FOREIGN PATENT DOCUMENTS

WO    WO 98/05274    2/1998

OTHER PUBLICATIONS

Baldick, H. et al., "Bioactive Glass Increases Alkaline Phosphatase Activity in Rat Marrow Stromal Cells In Vitro," *Transactions 5th World Biomaterials Conference,* Toronto, Canada, May 29–Jun. 2, 1996.

El–Ghannam et al., "Bioactive material template for in vitro synthesis of bone," *J. Biomed. Mat. Res.,* 1995, 29, 359–370.

Healy et al., "Hydration and preferential molecular adsorption on titanium in vitro," *Biomaterials,* 1992, 13(8), 553–561.

Hedman et al., "Design of an Intervertebral Disc Prosthesis," *Spine,* 1991, 16(Supp. 6), 256–260.

Hou et al., "Lumbar Intervertebral Disc Prosthesis," *Chinese Med. J.,* 1991, 104(5), 381–386.

Lee et al., "Development of a Prosthetic Intervertebral Disc," *Spine,* 1991, 16(Supp. 6), 253–255.

Lee et al., *35th Annual Meeting of the Orthopaedic Research Society,* Las Vegas, Nevada, Feb. 6–9, 1989.

McMillin, C.R. et al., *20th Annual Meeting of the Society for Biomaterials,* Abstract, 1994.

Qui, Q. et al., "Bone Growth on Sol–Gel Calcium Phosphate Thin Films in Vitro," *Cells and Materials,* 1993, 3(4), 351–360.

Sabolinski, "Cultured skin as a 'smart material' for healing wounds: experience in venous ulcers," *Biomaterials,* 1996, 17, 311–320.

Schepers et al., "Bioactive glass particulate material as a filler for bone lesions," *J. Oral Rehab.,* 1991, 18, 439–452.

Urbaniak et al., "Replacement of Intervertebral Discs in Chimpanzees by Silicone–Dacron Implants: A Preliminary Report," *Bio. J. Med. Mater. Res. Sym.,* 1973, 4, 165–168.

White et al., *Clinical Biomechanics of the Lumbar Spine,* Churchill Livingston, London, 1989.

PCT International Search Report dated Oct. 29, 1997, 4 pages.

* cited by examiner

*Primary Examiner*—David M. Naff
(74) *Attorney, Agent, or Firm*—Woodcock Washburn LLP

(57) ABSTRACT

Methods and materials are provided for reforming degenerated intervertebral discs of the spine of a vertebrate and in particular the spine of a human. Tissue is evacuated from the nucleus pulposus portion of a degenerated intervertebral disc space, and a biodegradable substrate containing isolated intervertebral disc cells is implanted in the evacuated space for reformation of intervertebral disc tissue. Intervertebral disc cells are provided by digesting intervertebral disc tissue with collagenase and incubating the cells in a medium supplemented with hyaluronidase. The substrate may be bioactive so as to enhance cell function. Substrates include bioactive glass granules, polymer foams and the polymer foams coated with a bioactive gel material produced by a sol–gel process. A polymer foam is dipped into a sol resulting from combining a metal alkoxide precursor with water and acid, residual sol is evacuated from pores of the foam, and remaining sol contained by the foam is allowed to gel. The polymer of the foam may be poly(D,L-lactide-co-glycolide). A preferred bioactive gel material contains 70% $SiO_2$, 25% CaO and 5% $P_2O_5$.

9 Claims, 1 Drawing Sheet

PREPARATION OF POLYMER FOAM HAVING GELLED SOL COATING FOR INTERVERTEBRAL DISC REFORMATION

This Application is a division of application Ser. No. 09/314,511, filed May 19, 1999, now U.S. Pat. No. 6,240,926, which is a division of application Ser. No. 08/694,191, filed Aug. 8, 1996, now U.S. Pat. No. 5,964,807.

FIELD OF THE INVENTION

The present invention concerns methods and materials useful for reforming degenerated discs of the spine of a vertebrate and in particular the spine of a human.

BACKGROUND OF THE INVENTION

Back pain is one of the most frequently reported musculoskeletal problems in the United States. 80% of the adults will miss work at least three times in their career due to back pain. The most common factor causing low back pain is the degeneration of the disc. At the ages between 35 to 37, approximately a third of the US population have suffered from a herniated disc.

The main functions of the spine are to allow motion, transmit load and protect the neural elements. The vertebrae of the spine articulate with each other to allow motion in the frontal, sagittal and transverse planes. As the weight of the upper body increases, the vertebral bodies which are designed to sustain mainly compressive loads, increase in size caudally. The intervertebral disc is a major link between the adjacent vertebrae of the spine. The intervertebral disc, the surrounding ligaments and muscles provide stability to the spine.

The intervertebral discs make up about 20–33% of the lumbar spine length. They are capable of sustaining weight and transferring the load from one vertebral body to the next, as well as maintaining a deformable space to accommodate normal spine movement. Each disc consists of a gelatinous nucleus pulposus surrounded by a laminated, fibrous annulus fibrosus, situated between the end plates of the vertebrae above and below.

The nucleus pulposus contains collagen fibrils and water-binding glycosaminoglycans. At birth, the nucleus pulposus contains 88% water, however, this percentage decreases with age. This water loss decreases its ability to withstand stress. The annulus fibrosus consists of fibrocartilaginous tissue and fibrous protein. The collagen fibers are arranged in between 10 to 20 lamellae which form concentric rings around the nucleus pulposus. The collagen fibers within each lamella are parallel to each other and runs at an angle of approximately 60 degrees from vertical. The direction of the inclination alternates with each lamellae. This crisscross arrangement enables the annulus fibrosus to withstand torsional and bending loads. The end-plates are composed of hyaline cartilage, and are directly connected to the lamellae which form the inner one-third of the annulus.

When under compressive loads, the nucleus pulposus flattens and bulges out radially. The annulus fibrosus stretches, resisting the stress. The end-plates of the vertebral body also resist the ability of the nucleus pulposus to deform. Thus, pressure is applied against the annulus and end-plate, transmitting the compressive loads to the vertebral body. When tensile forces are applied, the disc is raised to a certain height straining the collagen fibers in the annulus. At bending, one side of the disc is in tension while the other side is in compression. The annulus of the compressed side bulges out.

When the disc is subjected to torsion, there are shear stresses which vary proportionally to the distance from the axis of rotation, in the horizontal and axial plane. The layer of fibers oriented in the angle of motion is in tension while the fibers in the preceding or succeeding layer are relaxed. Similarly in sliding, the fibers oriented in the sliding direction are in tension while the fibers in the other layers relax.

Repeated rotational loading initiates circumferential tears in the annulus fibrosus, which gradually form radial tears into the nucleus pulposus until the nucleus degrades within the disc. In addition to the water loss which occurs with age, more water is also lost due to nucleus rupture, thereby reducing its ability to resist compressive loads. As such, the annulus bulges. As the severity of the tear increases, much of the contents of the disc is lost leaving a thin space of fibrous tissue. This condition is called disc resorption.

Increasing disc collapse can cause facet subluxation and stenosis of the intervertebral foramen. Subsequently, the degenerative process involves the facet joints equally. As the annulus bulges out posteriorly into the spinal canal, the nerve root may be compressed causing sciatica. Pain is felt from the lower back to the buttocks and the leg. Following the rupture of the disc, excessive motions such as excessive extension or flexion can occur, resulting in spine segmental instability. The spine is thus more vulnerable to trauma. Herniation can occur due to disc degeneration or excessive load factors especially compression. Pain may result due to nerve root compression caused by protrusions.

The unstable phase of the degeneration progress allowing excessive movement may result in degenerative spondylolisthesis, which is a breakdown of posterior joints. The nerve is trapped between the inferior articular facet of the vertebrae above and the body of that below. Thus, sliding of a vertebral body on another damages the posterior joints due to fatigue and apply traction on the nerve root causing pain.

Surgical treatments for herniated disc include laminectomy, spinal fusion and disc replacement with prostheses.

At this time, 150,000 spinal fusion procedures are performed per year in the U.S. alone, and the numbers are growing exponentially. However, the results of spinal fusions are very varied. Some of the effects include non-unions, slow rate of fusion even with autografts, and significant frequency of morbidity at the graft donor site. In addition, even if the fusion is successful, joint motion is totally eliminated. Adverse effects of spinal fusions have also been reported on adjacent unfused segments such as disc degeneration, herniation, instability spondylolysis and facet joint arthritis. A long-term follow-up of lower lumbar fusions in patients from 21 to 52 years of age found that 44% of patients with spinal fusions were currently still experiencing low-back pain and 57% had back pain within the previous year. 53% of the patients tracked were on medication, 5% had late sequela secondary surgery, 15% had a repeat lumbar surgery, 42% had symptoms of spinal stenosis, and 45% had instability proximal to their fusion. This clinical data shows that significant long-term limitations are associated with spinal fusion.

An alternative to spinal fusion is the use of an intervertebral disc prosthesis. Ideally, a successful disc prosthesis will simulate the function of a normal disc. The disc replacement must be capable of sustaining weight and transferring load from one vertebral body to the next. It should be robust enough not to be injured during movement and should maintain a deformable space between the vertebral body to accommodate movement.

Disc protheses should last for the lifetime of the patient, should be able to be contained in the normal intervertebral disc space, should have sufficient mechanical properties for normal body function, should be able to be fixed to the vertebrae adjacent to the disc, should be possible to implant, should not cause any damage should the disc fail, and should be biocompatible.

There are at least 56 artificial disc designs which have been patented or identified as being investigated, McMillin C. R. and Steffee A. D., 20th Annual Meeting of the Society for Biomaterials (abstract) (1994), although not all these devices have actually been made or tested. They can be divided into two main categories. Lee et al., Spine, Vol. 16, 253–255(1991). A first class includes devices for nucleus pulposus replacements which includes metal ball bearing, a silicone rubber nucleus, and a silicone fluid filled plastic tube. Devices for total or subtotal replacement of the disc have also been proposed such as a spring system, low-friction sliding surfaces, a fluid filled chamber, elastic disc prosthesis and elastic disc encased in a rigid column.

An example of total disc replacement is described by Urbaniak et al., Bio. J. Med. Mater. Res. Sym., Vol. 4, 165–186 (1973) who developed and tested, using chimpanzees, an intervertebral disc device made of a central silicone layer sandwiched between two layers of Dacron embedded in the silicone. The open-mesh Dacron was chosen to allow tissue ingrowth for fixation to the adjacent vertebrae. While spinal mobility was restored and the device tolerated by the host, due to inexact fit of the device, bone resorption and reactive bone formation were observable. Loose fibrous tissue also indicated possible movement of the device.

Hou et al., Chinese Medical Journal, Vol. 104(5), 381–386 (1991), developed a disc implant made of silicone rubber which restored normal disc function. However, the presence of fibrous tissue surrounding the implant indicated possible movement of the device.

The SB Charite intervertebral disc endoprosthesis, White and Panjabi, Clinical biomechanics of the lumbar spine, Churchill Livingstone, London (1989), which has been tested clinically, is fabricated from a biconvex polyethylene core sandwiched between two concave-molded titanium end-plates. However, the endoprosthesis shows insufficient mechanical performance and unlikely long-term bone fixation to the device.

Two types of disc prostheses were developed and evaluated by Lee et al., 35th Annual Meeting of the Orthopaedic Research Society, Las Vegas, Nev., Feb. 6–9, 1989; Dacron fiber-reinforced polyurethane elastomer (reinforcement located for the annulus section), and a prosthesis made from thermoplastic polymer which is increasingly rigid moving from the nucleus out to the end-plates. Yet another design is made of cobalt-chromium-molybdenum (Co—Cr—Mo) alloy by Hedman et al., Spine, Vol. 16, 256–60 (1991).

U.S. Pat. No. 4,911,718 (Lee et al.), U.S. Pat. No. 5,002,576 (Fuhrmann et al.), U.S. Pat. No. 4,911,718 (Lee et al.) and U.S. Pat. No. 5,458,642 (Beer et al.) also teach permanent intervertebral disc endoprostheses for total disc replacement.

All of foregoing intervertebral disc prostheses, however, merely replace all or a part of the disc with synthetic materials which must remain in place ad infinitum. These prostheses are generally permanent implants which require observation of long term biologic responses throughout the life of the prothesis. Furthermore, discs that are not comprised of biocompatible material may be rejected by the patient.

Procedures by which the tissues of the intervertebral disc are made to reform or replace the degenerated tissue of the intervertebral disc, would be highly desirable and a significant improvement over the current state of the art which presently use such permanent implants. Although efforts at tissue-engineering have been reported, no one has, until now, accomplished reformation of intervertebral disc tissue.

Repair of skin tissue has been achieved. For instance, skin deficiencies which arise in severely burnt patients or in decubitus wounds of diabetic patients have been so treated. Sabolinski, Biomaterials, Vol. 17, 311–320 (1996). Cells are seeded onto templates of either resorbable or non-resorbable material. Once tissue begins to form the templates are dressed onto the site in need of treatment. Tissue engineering of the skin, however, is significantly different from tissue engineering of the intervertebral disc because tissue compositions differ significantly. In addition, the mechanical requirements of engineered skin tissue are significantly different from those of intervertebral disc tissue.

Some intervertebral disc prostheses provide for regrowth of the intervertebral disc and concurrent resorption of the prothesis. For example, U.S. Pat. Nos. 4,772,287 and 4,904,260 (Ray et al.) teach prosthetic discs having an outer layer of strong, inert fibers intermingled with bioresorbable materials which attract tissue ingrowth. However, this prosthesis is purely a synthetic material at the time of implantation and does not include any cells or developing tissue. In addition, it provides only partial resorption and the problems associated with permanent implants remain.

U.S. Pat. Nos. 5,108,438 and 5,258,043 (Stone) teach a porous matrix of biocompatible and bioresorbable fibers which may be interspersed with glycosaminoglycan molecules. The matrix serves as a scaffold for regenerating disc tissue and replaces both the annulus fibrosus and nucleus pulposus. However, replacement of this much tissue is a relatively invasive procedure which requires lengthy recovery time. Furthermore, these matrices do not use any cells to stimulate tissue recovery nor is there any incipient tissue formation in this device at the time of implantation.

Various materials have been seeded with cells in order to facilitate cell function including proliferation and extracellular matrix synthesis. For instance, El-Ghannam, et al., Journal of Biomedical Materials Research, Vol. 29, 359–370 (1974), teaches in vitro synthesis of bone-like tissue using bioactive glass templates. Schepers, et al., J. Oral Rehab., Vol. 18, 439–452 (1991), analyzed the use of bioactive glass as fillers for bone lesions. Also, porous polymeric matrices have been used. The polymers include poly(lactic acid), poly(glycolic acid) and their co-polymers. However, these polymers have not been taught to be appropriate substrates for intervertebral disc cells which until now have not been used to seed implants of any sort.

Ideally, intervertebral disc treatment would guide and possibly stimulate the reformation of the tissue of affected intervertebral disc, especially nucleus pulposus and annulus fibrosus tissue. It could also biodegrade while allowing concurrent nucleus pulposus and annulus fibrosus tissue ingrowth, thereby providing for disc regeneration. Such an intervertebral disc material which is biodegradable while still satisfying the mechanical requirements of an intervertebral disc, has not been available until now.

OBJECTS OF THE INVENTION

An object of the present invention is to provide a method of inducing and/or guiding intervertebral disc reformation using biodegradable support substrates.

In yet another object of the present invention is provided biodegradable substrates useful for intervertebral disc tissue reformation.

Still another object of the invention is to provide material useful for guiding and/or stimulating intervertebral disc tissue reformation.

Another object of the invention is to provide methods of culturing intervertebral disc cells.

SUMMARY OF THE INVENTION

Figure 1:
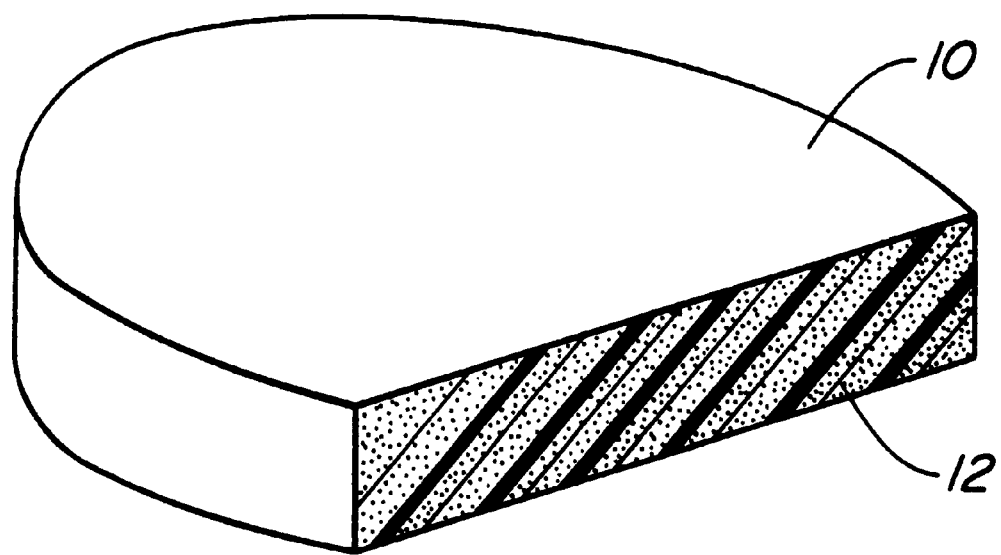
FIG. 1 is a perspective view of an exemplary hybrid material of the present invention.

In accordance with methods of the present invention there are provided methods for repairing damaged or degenerated intervertebral discs. These methods comprise evacuating tissue from the nucleus pulposus portion of a degenerated intervertebral disc space, preparing hybrid material by combining isolated intervertebral disc cells with a biodegradable substrate, and implanting the hybrid material in the evacuated nucleus pulposus space. In accordance with methods of the invention intervertebral disc cell growth is guided and/or stimulated and intervertebral disc tissue is reformed.

Methods of culturing intervertebral disc cells are also provided in some aspects of the invention whereby intervertebral disc tissue is digested with collagenase and incubated in medium supplemented with hyaluronidase.

In still other aspects of the invention biodegradable substrates are provided comprising polymer foam coated with bioactive materials, which substrates are useful for intervertebral disc tissue reformation.

In yet another aspect of the invention are provided hybrid materials for reforming degenerate intervertebral disc tissue. The hybrid materials can be made in the form of shaped bodies comprising biodegradable substrate and intervertebral disc-cells.

DETAILED DESCRIPTION OF THE INVENTION

The present invention is directed to methods of inducing intervertebral disc repair by reformation of intervertebral disc tissue. By implanting a hybrid material comprising intervertebral disc cells and a biodegradable support substrate into the intervertebral disc space, ingrowth of intervertebral disc cells is induced. Thus, the present invention provides methods of inducing self-regeneration of viable tissue and functional joints.

Methods of the present invention are useful to treat vertebrates suffering from degenerated intervertebral disc conditions, and in particular may be used to treat humans with such conditions.

A degenerated intervertebral disc has lost or damaged some or all of its intervertebral disc tissue, primarily including its nucleus pulposus tissue, due to any number of factors discussed herein, including age and stress due to rotational loading. Degenerated discs vary in severity from bulging discs to herniated or ruptured discs. Patients suffering from a degenerated disc experience a number of symptoms which include pain of the lower back, buttocks and legs and may also include sciatica and degenerative spondylolysis. In accordance with methods of the present invention reformation or regeneration of intervertebral disc tissue occurs in situ, replacing lost or damaged tissue and resulting in amelioration or elimination of the conditions associated with the degenerated disc.

In accordance with the present invention hybrid materials used to induce and/or guide reformation of intervertebral disc tissue comprise biodegradable substrates. Biodegradable means that the substrate degrades into natural, biocompatible byproducts over time until the substrate is substantially eliminated from the implantation site and, ultimately, the body. Preferably in accordance with methods of the present invention, the rate of biodegradation of the substrate is less than or equal to the rate of intervertebral disc tissue formation such that the rate of tissue formation is sufficient to replace the support material which has biodegraded.

In some aspects of the present invention the biodegradable substrate may be bioactive. Bioactive, as used herein, is meant to refer to substrates which enhance cell function as compared to cell function of the same cell type in the absence of the substrate. For instance, bioactive glass granules have been shown to enhance cell growth of typical bone cells. Schepers et al., U.S. Pat. No. 5,204,106. In addition, dense bioactive glass discs have been found to enhance osteoprogenitor cell differentiation beyond even those levels of enhanced differentiation elicited by bone morphogenic protein. H. Baldick, et al., Transactions 5th World Biomaterials Conference, Toronto, II-114 (June, 1996).

The biodegradable substrate must also have sufficient mechanical strength to act as a load bearing spacer until intervertebral disc tissue is regenerated. In addition, the biodegradable substrate must be biocompatible such that it does not elicit an autoimmune or inflammatory response which might result in rejection of the implanted hybrid material.

Biodegradable support substrates useful in methods of the present invention include bioactive glass, polymer foam, and polymer foam coated with sol gel bioactive material.

In accordance with some methods of the present invention bioactive glass is employed as a substrate. Bioactive glass is described in U.S. Pat. No. 5,204,104, incorporated by reference herein in its entirety. The bioactive glass contains oxides of silicon, sodium, calcium and phosphorous in the following percentages by weight: about 40 to about 58% $SiO_2$, about 10 to about 30% $Na_2O$, about 10 to about 30% $CaO$, and 0 to about 10% $P_2O_5$. In preferred embodiments of the invention the nominal composition of bioactive glass by weight is 45% $SiO_2$, 24.5% $Na_2O$, 24.5% $CaO$ and 6% $P_2O_5$ and is known as 45S5 bioactive glass. Bioactive glass may be obtained from commercial sources such as Orthovita, Inc. (Malvern, Pa.).

Granule size of the bioactive glass is selected based upon the degree of vascularity of the affected tissue and generally will be less than about 1000 $\mu$m in diameter. In some embodiments of the present invention it is preferred that the bioactive glass granules be from about 200 $\mu$m to about 300 $\mu$m in diameter. In still other embodiments of the present invention granule size is from about 50 $\mu$m to about 100 $\mu$m.

In some embodiments of the present invention bioactive glass has pores. Percent density (100%-percent porosity) of less than about 80% may be used in some aspects of the invention. Percent density of about 10% to about 68% can be used for other aspects of the invention. In some aspects of the present invention the pore size should be less than about 850 $\mu$m in diameter while about 150 $\mu$m to about 600 $\mu$m pore diameter is preferred.

One method of preparing porous bioactive glass is by mixing bioactive glass granules of a desired size with sieved sacrificial agent camphor particles of a desired amount and size. The camphor sublimates during sintering leaving pores in the sintered glass. Thus, the average particle size and weight percent of the camphor particles is chosen to optimize the pore size and percent porosity, respectively, of the glass. In some aspects of the invention particle size may be less than about 850 μm in diameter while about 150 μm to about 600 μm is preferred. Thereafter the glass may be treated with any aqueous buffer solution containing ions, the identity and concentration of which is found in interstitial fluid. Said treatments result in the formation of a calcium phosphate rich layer at the glass surface. Typical buffers include those prepared as described by Healy and Ducheyne, *Biomaterials*, Vol. 13, 553–561 (1992), the subject matter of which is incorporated herein by reference in its entirety.

In still other aspects of the present invention the support substrate comprises polymer foam. Polymer foam useful in these aspects of the invention are biocompatible and include polyglycolide (PGA), poly(D,L-lactide) (D,L-PLA), poly (L-lactide) (L-PLA), poly(D,L-lactide-co-glycolide), (D,L-PLGA),poly(L-lactide-co-glycolide) (L-PLGA), polycaprolatone (PCL),polydioxanone, polyesteramides, copolyoxalates, and polycarbonates. D,L-PLGA, which is preferred in some embodiments of the invention, may comprise 50% polylactide and 50% polyglycolide. About 75% polylactide and about 25% polyglycolide is still more preferred although it is anticipated that ratios may be varied to optimize particular features of the individual polymers. For instance, the mechanical strength of a polymer may be adjusted by varying the percentage of PLA and the percentage of PGA may be adjusted to optimize cell growth.

In some aspects of the invention polymer foam is coated with sol gel bioactive material. Sol gel materials include glasses and ceramics. Such bioactive compound are prepared by mixing a desired polymer foam with NaCl to create the desired porosity and pore size. Thereafter, the polymer, including the pores and interstices, is coated with sol gel material.

Sol gel glass is prepared by combining a metal alkoxide precursor with water and an acid catalyst to produce a gel. A typical process is described in U.S. Ser. No. 08/477,585 (U.S. Pat. No. 5,591,453) which is incorporated by reference herein in its entirety. Once dried, the gel consists mostly of metal oxide with a glass consistency. Sol gel bioactive material may be comprised of from about 60 to about 100% silicon dioxide, up to about 40% calcium oxide and up to about 10% diphosphorous pentoxide. A final product of 70% $SiO_2$, 25% CaO, and 5% $P_2O_5$ is preferred in some methods of the present invention although the concentration of each may be adjusted to optimize critical features of the sol gel. Other sol gel materials may be prepared by methods known in the art. For instance, Qui, Q., et al., *Cells and Materials*, Vol. 3, 351–60 (1993), incorporated by reference herein in its entirety, discusses methods of preparing calcium phosphate sol gel bioactive material.

To coat the polymer, the polymer foam is dipped into the sol during the sol gelation phase. The sol-filled foam is then placed in a syringe filter and the sol is pulled through the foam by creating a vacuum below using the syringe. Thus, the polymer is substantially coated with sol gel, with residual sol gel being evacuated from the polymer matrices. While it is preferred that most or all of the polymer surfaces, including the surfaces of the pores and interstices, be coated with sol gel bioactive glass, polymers which are only partially coated with sol gel bioactive glass may also be useful in some aspects of the present invention. It is desired in some embodiments of the invention that greater than about 50% of the polymer surface be coated.

To prepare the hybrid material, intervertebral disc cells are combined with biodegradable substrate material. Intervertebral disc cells may be isolated from tissue extracted from any accessible intervertebral disc of the spine. For instance, tissue may be extracted from the nucleus pulposus of lumbar discs, sacral discs or cervical discs. Preferably, intervertebral disc cells are primarily nucleus pulposus cells. In some embodiments it is preferred that disc cells are at least 50% nucleus pulposus cells while 90% nucleus pulposus cells is still more preferred. Cells may be obtained from the patient being treated, or alternatively cells may be extracted from donor tissue.

The present invention provides advantages over prior art methods in that the entire degenerated disc need not be removed to treat a degenerated disc. Rather, only the nucleus pulposus tissue need be evacuated from the degenerated intervertebral disc. Degenerated nucleus pulposus refers to a region of the intervertebral disc where the tissue has severely reduced mechanical properties or which has lost some or most of the nucleus pulposus tissue. The present invention thus provides a less invasive procedure than that of the prior art. In addition, the methods and hybrid materials of the present invention prompt biological repair of normal tissue in the disc which will result in better long term results than that obtained with synthetic prostheses.

Evacuation of the degenerated intervertebral disc tissue, and primarily the nucleus pulposus tissue, is performed using known surgical tools with procedures developed to meet the needs of the present invention. Generally an incision or bore is made at the lateral edge in the annulus fibrosus and the intervertebral disc tissue is extracted from the nucleus pulposus via, for example, the guillotine cutting approach. The tissue may be extracted using a scalpel, bore, or curette. Alternatively, tissue may be aspirated. Ideally, the annulus fibrosus, or significant portions thereof, are left intact. It is preferred for instance, that at least 50% of the annulus fibrosus remain intact. It is still more preferred that at least 85% of the annulus fibrosis remain intact. Arthroscopic techniques are most preferred in accordance with methods of the present invention.

Similar surgical techniques are utilized to extract intervertebral disc tissue from other, non-degenerate intervertebral discs of the spine of the patient or donor. For instance, similar techniques may be used to obtain intervertebral tissue from sacral discs. Minor modifications necessary to tailor the procedure to a particular region of the spine would be appreciated by those skilled in the art.

Where there is lag time between tissue evacuation and implantation of the hybrid material, the evacuated space may be temporarily filled with gel foam or other load bearing spacers known in the art.

Intervertebral disc cells are isolated from extracted tissue. Generally, tissue is fragmented and treated with enzymes such as collagenase to disaggregate the cells into individual cells. Preferably isolated cells are primarily nucleus pulposus cells with 50% nucleus pulposus cells being preferred and 90% nucleus pulposus cells being more preferred. The cells are isolated using centrifugation. Cells may then be combined with a biodegradable substrate and implanted into the evacuated nucleus pulposus. Alternatively, isolated intervertebral disc cells may be cultured alone or seeded onto a biodegradable substrate and cultured together with the biodegradable substrate for later implantation.

In some aspects of the present invention the hybrid material may also include factors to enhance cell growth. For instance, TGF-β and EGF may be added to the hybrid material to enhance cell growth. Cells may be incubated alone or seeded on a substrate in a tissue culture medium such as Dulbeccols Modified Eagle Medium (DMEM) (pH 7.0), which may be supplemented with serum such as heat-inactivate fetal bovine serum. Antifungal and antibacterial agents may also be added. In preferred methods of the present invention cells are incubated with about 0.5% to about 1.5% hyaluronidase.

In some aspects of the present invention the end plate may be partially decorticated to enhance vascularization. Thereafter, cells may be implanted or alternatively, after cell attachment, hyaluronidase is removed and incubation is resumed with a medium supplemented with 0.001% ascorbic acid in the absence of hyaluronidase. Medium supplemented with 0.0025% ascorbic acid is used to replenish the cell solutions.

Hybrids of intervertebral disc cells and biodegradable substrate may then be implanted into the evacuated intervertebral disc space using surgical procedure such as described above.

Hybrid materials are provided by the present invention. Such hybrids can then be shaped for insertion into the intervertebral disc space of a patient. Exemplary FIG. 1 shows a shaped hybrid material comprising biodegradable substrate and intervertebral cells. Intervertebral cells are located on the outer surface 10 and on the surfaces of the pores and interstices 12 of the shaped substrate. It should be noted that FIG. 1 depicts one possible embodiment and should not be construed as limiting the invention in any way.

The substrate should generally have a rectangular shape. A cylindrical pad shape is also envisioned.

The following examples are illustrative but are not meant to be limiting of the present invention.

EXAMPLES

Example 1
Evacuation of Nucleus Pulposus

Mature New Zealand rabbits weighing 4–5 kg are used. For each rabbit, L4–L5 or, when possible L4–L5 and L5–L6 disc spaces are accessed as those are the biggest sections. The anesthetics Ketamine, HCl 30 mg/kg, and Xylazine 6 mg/kg, are administered intramuscularly. Using a paraspinal posterolateral splitting approach, the large cephalad-facing transverse process of the lumbar spine is identified and removed with a rongeur. The intervertebral disc can then be seen. An incision is made in the annulus fibrosus. Using a high-power surgical microscope, the nucleus pulposus tissue is scraped out carefully with a curette. The space is then packed with gel foam. The rabbit is closed provisionally.

Example 2
Isolation of Intervertebral Disc Cells

Intervertebral disc tissue is obtained as described in Example 1 or from an amputated tail section. Under aseptic condition, the intervertebral disc tissue is diced with a scalpel and placed in a T25 tissue culture flask with Dulbecco's Modified Eagle Medium (DMEM) adjusted to pH 7.0, supplemented with 10% heat inactivated fetal bovine serum and 1% penicillin/streptomycin (TCM). The tissue is then treated with 0.25% collagenase for two hours at 37° C. An equal amount of TCM to collagenase is added to stop treatment. The mixture is centrifuged at 1000 r/min for 10 minutes and supernatant is discarded. TCM is added and the mixture is filtered to remove debris. The mixture is again centrifuged and supernatant discarded. Cells are resuspended in TCM supplemented with 1% hyaluronidase (400 u/ml).

Example 3
Culture of Intervertebral Disc Cells

Cells are cultured in TCM supplemented with 1% hyaluronidase (400 u/ml) at 37° C. in 5% CO2/95% air. Once cells attach medium is changed to TCM supplemented with 0.001% ascorbic acid in the absence of hyaluronidase. Cells are resuspended in fresh medium supplemented with 0.0025% ascorbic acid every 3 days.

Example 4
Preparation of Bioactive Glass

Bioactive glass granules (45S5) having diameters of 40 $\mu$m to 71 $\mu$m can be obtained from Orthovita, Inc. (Malvern, Pa.). Prior to implantation or addition to cell culture, the specimens are sterilized in ethylene oxide.

Example 5
Preparation of Sintered Porous Bioactive Glass

Bioactive glass granules having diameters of 40 $\mu$m to 71 $\mu$m can be obtained from Orthovita, Inc. (Malvern, Pa.). The glass granules are mixed with 20.2 weight % sieved sacrificial agent camphor $C_{10}H_{16}O$ with grain size of 300 $\mu$m to 500 $\mu$m. The mixture is mechanically mixed overnight, and cold pressed at 350 MPa. The disc obtained is heat treated at 575° C. for 45 minutes. The heating rate is 10° C./min. It is then left to cool at room temperature. The disc is immersed in acetone for 30 minutes and dried at 37° C. The disc is cut to the desired dimensions using a diamond-wheel saw. The disc is washed in acetone for 15 minutes. The specimen is then conditioned in tris buffer with electrolytes added (TE) (El-Ghannam, et al., *Journal of Biomedical Materials Research*, Vol. 29, 359–370 (1974)), for 2 days to obtain the desired formation of calcium phosphate-rich layer at the glass surface. The specimen is rinsed with methanol and dried at 37° C. The specimen is analyzed using scanning electron microscopy (SEM), Fourier Transform Infrared (FTIR) spectroscopy and X-ray diffraction (XRD). Prior to implantation or introduction to cell culture, the specimen is sterilized in ethylene oxide.

Example 6
Preparation of Polymer Foam 3 g of NaCl with particle sizes 300 $\mu$m to 500 $\mu$m, and 2 g of D,L-PLGA 75/25 (75% polylactide/25% polyglycolide) polymer foam were mixed. The dispersion is vortexed and cast in a 5 cm petri dish. The solvent is allowed to evaporate from the covered petri dish for 48 hrs. To remove residual amounts of chloroform, the petri dish is vacuum-dried at 13 Pa for 24 hrs. The material is then immersed in 250 ml distilled deionized water at 37° C. for 96 hrs. The water is changed every 12 hrs to leach out the salt. The salt-free membrane is air-dried for 24 hrs, followed by vacuum-drying at 13 Pa for 48 hrs. The material is then cut to the desired geometry with a razor blade. The membrane is stored in a desiccator under vacuum. The specimens are analyzed using SEM. The specimen will have 60% pore density with pore sizes 300 to 500 $\mu$m. Prior to implantation or introduction into cell culture, the specimens are sterilized in ethylene oxide.

Example 7
Preparation of Polymer Foam coated with Sol Gel Bioactive Glass

Tetramethylorthosilane (TMOS),calcium methoxyethoxide and triethyl phosphate are mixed for 5 minutes in an argon atmosphere using a magnetic stirrer. Respective amounts of each are chosen such that the resulting product is 70% $SiO_2$-25%CaO-5%$P_2O_2$ (upon drying). They are mixed using a magnetic stirrer for 5 min. The PLGA polymer foam prepared according to Example 5 is dipped into the sol approximately halfway to gelation. The foam is dipped 2 to 3 times to make sure that the sol completely fills the polymer foam. The sol-filled foam is then placed in a syringe filter with appropriate filter pore size which only allows the sol to flow through. This syringe filter is attached to a syringe. The sol is pulled through the foam by creating a vacuum below using the syringe. EDAX and SEM are used to analyze pore size, porosity and the thickness/uniformity of the sol gel bioactive glass coating. Prior to implantation or introduction to cell culture, the specimens are sterilized in ethylene oxide.

Example 8
Cell Phenotype

Cell phenotype of cells cultured in accordance with the method of Example 3 is examined. Immunofluorescent staining of cells shows positive staining for proteoglycan and collagen type II, markers of intervertebral disc cell phenotype. Substantially negative staining for collagen I, a annulus fibrosus marker, was also observed.

Example 9
Cell Reversion

Intervertebral disc cells cultured as described in Example 3 are tested for reversion. Cells are placed in Eppendorf tube with TCM and spun down to form a pellet. Cell histology is examined after 4, 8 and 12 days by washing the pellet and fixing it with 70% ethanol. The cells are dehydrated, embedded and cut. The sample is stained with hematoxylin-eosin and toluidine blue.

The histology of cultured cells is compared to the histology of nucleus pulposus tissue prepared immediately upon retrieval. Histology of the cells evidences a reversion to the original morphology of the cells.

Example 10
Implantation of Biodegradable Substrate

Cells are prepared in accordance with Examples 2 and 3. Cells are counted. Biodegradable substrates prepared as described in Examples 4–7 each placed in a tissue culture dish and immersed in TCM for 1 hour. The cells are seeded onto each of the sterile biodegradable substrates prepared as described in Examples 4–7 in TCM with hyaluronidase and left to attach for at least one hour before flooding the dish with TCM. Cells are incubated overnight. Attachment is detected using SEM.

The rabbit treated as described in Example 1 is reopened per surgical technique described in Example 1, and the intervertebral disc space accessed. The gel foam is retrieved and the cell-biodegradable substrate hybrid material inserted in place. The wound is closed.

Example 11
Effect on Neurological Function

Regular post-operative neurological functions are evaluated to examine the subject for any spinal injury such as lameness. The effect of the hybrid material on the behavior of the disc can be observed and generally compared by taking radiographs of the spine immediately pre-operation, post-operation and at 1 month time periods until the animal is sacrificed.

Example 12
Histological Analysis

Histological analysis is performed to determine cell ingrowth, cell types, tissue morphology, and absence of inflammation. To this end, the retrieved disc is fixed in 70% ethanol and dehydrated. After embedding in methyl methacrylate, sections are cut with a diamond saw, ground, polished with silicon carbide paper and diamond paste, and stained. Histology is done on normal discs and discs retrieved at the various time periods. Analysis will show ingrowth of cells with concurrent degradation of implanted hybrid material with little to no inflammation.

What is claimed is:

1. A method of making a bioactive substrate comprising a porous polymer foam coated with a bioactive gel material, wherein the bioactive gel material is produced by a sol-gel process comprising combining a metal alkoxide precursor with water and an acid catalyst to produce a sol and allowing the sol to gel, comprising the steps of:

dipping the porous polymer foam into the sol whereby pores of the polymer foam are filled with the sol, evacuating residual sol from the pores of the polymer foam, and allowing remaining sol contained by the porous polymer foam to gel to obtain the porous polymer foam coated with the bioactive gel material, wherein the bioactive gel material penetrates the pores of the polymer foam and at least about 50% of the surface of the polymer foam, which includes the pores, is coated with the bioactive gel material.

2. The method of claim 1 wherein the pores of the polymer are evacuated by creating a suction vacuum.

3. The method of claim 1 wherein the porous polymer foam is polyglycolide (PGA), poly(D,L-lactide) (D,L-PLA) poly(L-lactide) (L-PLA), poly(D,L-lactide-co-glycolide) (D,L-PLGA), poly(L-lactide-co-glycolide) (PLGA), polycaprolatone (PCL), polydioxanone, polyesteramides, copolyoxalates, polycarbonates, or combinations thereof.

4. The method of claim 3 wherein the porous polymer foam is poly(D,L-lactide-co-glycolide).

5. The method of claim 1 wherein the bioactive gel material is comprised of from about 60% to about 100% $SiO_2$, up to about 40% CaO; and up to about 10% $P_2O_5$.

6. The method of claim 1 wherein the bioactive gel material has the nominal composition 70% $SiO_2$, 25% CaO; and 5% $P_2O_5$.

7. The method of claim 1 wherein the bioactive gel material has a pore size of leass than about 850 μm.

8. The method of claim 1 wherein the bioactive gel material has a percent density less than about 80%.

9. The method of claim 1, further comprising the step of adding cell growth enhancers.

* * * * *